United States Patent [19]

Tsumura et al.

[11] Patent Number: 5,302,685

[45] Date of Patent: Apr. 12, 1994

[54] METHOD FOR PREPARING ORGANOPOLYSILOXANE POWDER

[75] Inventors: Hiroshi Tsumura, Annaka; Nobuhiko Kodana, Tomioka; Hidehiko Aonuma; Kenichi Isobe, both of Annaka, all of Japan

[73] Assignee: Shin-Etsu Chemical Co., Ltd., Tokyo, Japan

[21] Appl. No.: 77,593

[22] Filed: Jun. 17, 1993

[30] Foreign Application Priority Data

Jun. 18, 1992 [JP] Japan .................................. 4-184524

[51] Int. Cl.$^5$ .......................... C07F 7/08; C08G 77/06
[52] U.S. Cl. ....................................... 528/33; 556/462; 203/47; 203/48; 203/91; 204/8
[58] Field of Search .......................... 556/462; 528/33; 203/47

[56] References Cited

U.S. PATENT DOCUMENTS

| | | | |
|---|---|---|---|
| 4,739,026 | 4/1988 | Riederer et al. | 556/462 X |
| 5,086,145 | 2/1992 | Morimoto et al. | 556/462 X |
| 5,130,400 | 7/1992 | Pachaly | 528/33 X |

Primary Examiner—Paul F. Shaver
Attorney, Agent, or Firm—Millen, White, Zelano & Branigan

[57] ABSTRACT

Organopolysiloxane powder is prepared from an organopolysiloxane solution by admitting the organopolysiloxane solution into a planetary-screw mixer and agitating the solution at a sufficient temperature to allow a low-boiling liquid component to evaporate from the solution, thereby separating the low-boiling liquid component from the solution.

9 Claims, 2 Drawing Sheets

METHOD FOR PREPARING ORGANOPOLYSILOXANE POWDER

FIELD OF THE INVENTION

This invention relates to a method for preparing organopolysiloxane powder by evaporating and removing a low-boiling liquid component from an organopolysiloxane solution.

BACKGROUND OF THE INVENTION

Organopolysiloxane powder has been used as resin modifiers and paint additives and is expected to find wider applications as elastomer reinforcements and cosmetic additives. Organopolysiloxanes are solid in pure form. The organopolysiloxanes, which are insoluble in solvents, for example, have a three-dimensional molecular structure with a high degree of polymerization, generally form with organic solvents a slurry in which they are dispersed in liquid as solids. If the solvent is water, solid organopolysiloxanes are afloat on water due to their water repellency.

Organopolysiloxane powder is prepared from such organopolysiloxanes by several conventional methods including a method of separating and collecting organopolysiloxane solids by filtration or centrifugal separation, followed by drying and a hot air drying method of directly drying organopolysiloxane solids through spray dryers and similar dryers. All the conventional well-known methods for preparing organopolysiloxane powder rely on drying. More specifically, Japanese Patent Application Kokai (JP-A) No. 13813/1985 or U.S. Pat. No. 4,528,390 discloses hydrolysis of a methyltrialkoxysilane in ammoniacal aqueous solution for condensation, followed by water washing and drying. Japanese Patent Publication (JP-B) No. 27579/1991 discloses condensation of a silane with a polysiloxane in an aromatic heterocyclic compound solvent followed by collection, washing and drying.

However, where organopolysiloxanes which are solid in pure form are dissolved in a solvent to form a solution in which no solids exist, typically when the solvent is the reaction medium which is used in synthesizing the organopolysiloxanes, the organopolysiloxanes cannot be separated by conventional means such as filtration and centrifugal separation. Organopolysiloxane powder is no longer obtained.

Even in this case, organopolysiloxane powder can be yielded evaporating and removing a low-boiling liquid component or solvent from the organopolysiloxane solution. The use of hot air dryers such as spray dryers provides a continuous operation which limits the residence time of the organopolysiloxane solution within the dryer, often failing to fully remove the low-boiling liquid component.

Batchwise operation can also be employed for evaporation. Evaporation in a container free of an agitator requires a long time because as solids precipitate, solid aggregates will grow, leading to a lowering of heat transfer. Full removal of a low-boiling liquid component is not expectable because the component can be retained in such solid aggregates. At the end of operation, the organopolysiloxane which is now solid cannot be discharged from the container.

Problems will arise even when evaporation is done while agitating the organopolysiloxane solution. Conventional commonly used agitating tanks equipped with paddle or anchor impellers allow some zones to stagnate as solids precipitate, allowing solid aggregates to grow in the stagnant zones as in the previous case. This results in a lowering of heat transfer, a longer time of operation, insufficient removal of low-boiling liquid component, and difficulty to empty the tank of the solidified organopolysiloxane. Additionally, when the solution reaches a semi-solid state immediately before solidification in the course of solvent evaporation, the rotating shaft experiences increased loads. Then a powerful motor must be used for agitation and the impeller must also be thick and rigid enough to withstand the loads.

It is then proposed to use helical ribbon impellers which have been conventionally used for mixing of high viscosity liquid and powder. Since the mixing tank associated with the helical ribbon impeller is of the same shape as the conventional agitating tanks, most of the above-mentioned problems remain unsolved.

The loads on the impeller can be reduced by using conical blenders or V-shaped blenders in which the tank itself rotates. These blenders, however, are of large size, require an increased cost for installation, and are rather inadequate for heating, evaporating and purposes.

Therefore, in a situation where organopolysiloxane solids are dissolved in a low-boiling liquid component or solvent to form a solution, an object of the present invention is to provide a method for preparing organopolysiloxane powder from the organopolysiloxane solution within a relatively short time and with a relatively reduced motive power, the resulting organopolysiloxane powder being characterized by full removal of the low-boiling liquid component and easy discharge from the tank.

SUMMARY OF THE INVENTION

Briefly stated, the present invention which attains the above and other objects provides a method for preparing organopolysiloxane powder from an organopolysiloxane solution using a conical vessel mixed by a simultaneous rotation and revolution of a screw or an agitater (referred to as a planetary-screw mixer) mixer whereby a low-boiling liquid component is separated from the solution by evaporation.

More specifically, the planetary-screw mixer used herein includes a generally conical hollow tank having a vertical center axis and an inner wall. The tank is equipped with agitating means which includes a rotating shaft having at least one impeller positioned at an inclination in close proximity to the tank inner wall. The agitating means functions to drive the shaft such that the shaft may rotate about its own axis and revolve about the center axis of the tank along the tank inner wall. The agitating means is operated for agitating the solution by rotation and revolution of the rotating shaft at a sufficient temperature to allow a low-boiling liquid component to evaporate from the solution, thereby evaporating and removing the low-boiling liquid component from the solution and yielding the organopolysiloxane powder.

In accordance with the method of the invention, organopolysiloxane powder which is fully free of the low-boiling liquid component is obtained within a relatively short time while requiring a relatively reduced motive power. The resulting organopolysiloxane powder is substantially free of aggregates and substantially free of the low-boiling liquid component and is thus sufficiently free flowing to discharge from the tank. The invention is particularly advantageous for obtaining in powder form an organopolysiloxane which contains a certain amount of a Q unit represented by $SiO_2$ and/or a T unit represented by $RSiO_{3/2}$ and forms a solid in the absence of a low-boiling liquid component, typically solvent.

In general, organopolysiloxanes are comprised of at least one unit selected from the group consisting of
(1) a unit represented by $SiO_2$ (referred to as a Q unit),
(2) a unit represented by $RSiO_{3/2}$ wherein R is independently a hydrogen atom or a substituted or unsubstituted monovalent hydrocarbon group having 1 to 12 carbon atoms (referred to as a T unit),
(3) a unit represented by $R_2SiO$ wherein R is as defined above (referred to as a D unit), and
(4) a unit represented by $R_3SiO_{\frac{1}{2}}$ wherein R is as defined above (referred to as a M unit). Among them, those organopolysiloxanes containing a certain amount or more of at least one of the Q and T units become solid in the absence of a low-boiling liquid component, typically solvent. For example, organopolysiloxanes consisting of M and Q units wherein R is methyl change as follows in accordance with the M/Q unit molar ratio.

| | |
|---|---|
| $M/Q < 1.0$ | solid |
| $1.0 \leq M/Q \leq 1.5$ | thermoplastic solid |
| $1.5 < M/Q$ | liquid |

Those organopolysiloxanes containing a M and/or D unit as a basic constituent unit are generally liquid or elastomeric at room temperature. Since the removal of low-boiling liquid component by evaporation in conventional agitating tanks is difficult to apply to those organopolysiloxanes which become solid as the low-boiling liquid component is removed by evaporation, the prior art procedure is limited to those organopolysiloxanes containing a M and/or D unit as a basic constituent unit and those organopolysiloxanes containing Q and/or T unit which melt and fluidize upon heating.

In accordance with the method of the invention adapted to subject an organopolysiloxane solution to evaporation in a specific agitating tank, even those organopolysiloxanes which contain a Q and/or T unit as a basic constituent unit and become solid as the low-boiling liquid component is removed by evaporation can be subjected to evaporation for removing the low-boiling liquid component therefrom. Furthermore, even if solids precipitate during evaporation, the rotation of the rotating shaft (inclusive of rotation about its own axis and revolution about the tank axis) provides grinding of solid precipitates at the same time as solids precipitate. The concurrent solid precipitation and pulverization allows the solvent removal-by-evaporation procedure to continue without growing solid aggregates. Then the low-boiling liquid component can be fully removed while maintaining good thermal conduction throughout the tank.

DESCRIPTION OF THE PREFERRED EMBODIMENT

In accordance with the method of the present invention, organopolysiloxane powder is prepared from an organopolysiloxane solution in a tank by evaporating and removing a low-boiling liquid component therefrom. The tank used is a generally conical or frustoconical hollow tank having a vertical center axis and an inner wall. The tank is equipped with agitating means which includes a rotating shaft having at least one impeller positioned at an inclination in close proximity to the tank inner wall. The impeller may be a screw-shaped impeller or a plurality of impellers. The agitating means functions to drive the shaft such that the shaft may rotate about its own axis and revolve about the center axis of the tank along the tank inner wall. After the organopolysiloxane solution is admitted into the tank, the agitating means is operated for agitating the solution by rotation and revolution of the rotating shaft and impeller at a sufficient temperature to allow a low-boiling liquid component to evaporate from the solution, thereby evaporating and removing the low-boiling liquid component from the solution and yielding the organopolysiloxane powder.

Figure 1:
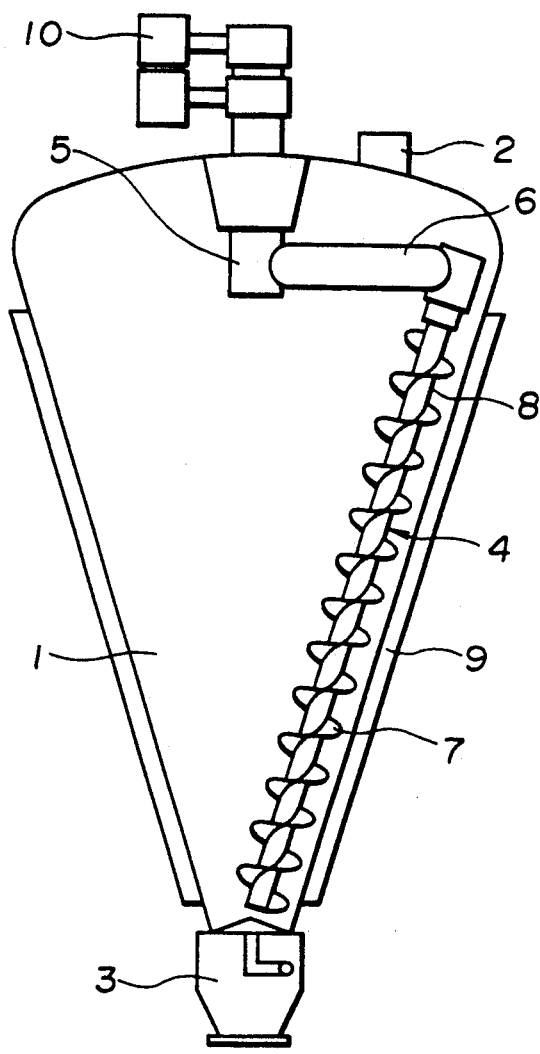
FIG. 1 is a schematic vertical cross-sectional view of one exemplary agitating tank used in the practice of the invention.

Referring to FIG. 1, there is illustrated one preferred embodiment of the agitating tank used herein. Illustrated is a fixed vessel type conical screw mixing tank equipped with a screw agitator which is known as a single arm planetary-screw mixer.

In FIG. 1, an inverted conical or frustoconical hollow tank 1 has a vertical center axis (not shown) and a conical or frustoconical inner wall. The tank 1 includes a vent 2 at its top and a discharge port 3 at its bottom. A heating jacket 9 surrounds the tank. The tank 1 can contain an organopolysiloxane solution. The tank 1 is equipped with an agitator 4 including a center shaft 5 in alignment with the tank center axis, an arm 6 coupled to the center shaft 5 for revolution therewith, and a rotating shaft 8 rotatably connected to the art 6 at its distal end. The rotating shaft 8 has a screw impeller 7 spirally extending around the shaft. The rotating shaft 8 extends between the arm end and the tank bottom and parallel to the tank inner wall with a close spacing therefrom. The rotating shaft 8 has an inclination in conformity to the conical inner wall. The center shaft 5 revolves together with the arm 6 and as a result, the rotating shaft 8 revolves about the tank center axis making a circular movement along the tank inner wall. Separately, the rotating shaft 8 is rotatable about its own axis. For the driving purpose, a motor assembly 10 is mounted at the top of the center shaft 5. The motor assembly 10 provides a motive force for driving the agitator for providing double actions including revolution of the rotating shaft 8 (or screw impeller 7) about the tank center axis and rotation of the rotating shaft 8 (or screw impeller 7) about its own axis.

The planetary-screw mixer of this type is commercially available as SV mixer from Shinko Pantech K. K. and Nauta mixer from Hosokawa Micron K. K.

Preferably the inclination of the tank inner wall or rotating shaft 8 is about 10° to 30° with respect to the vertical axis. Inclination in excess of 30° or gentle slope is less desirable in discharging the organopolysiloxane powder from the tank 1 through the discharge port 3 because some powder can remain in the tank. A tank with an inclination angle of less than 10° is vertically elongated and will undesirably require a space of an increase height for installation.

According to the invention, an organopolysiloxane solution is admitted into a planetary-screw mixer as mentioned above and agitated at elevated temperature by double actions of the screw impeller including rotation about its own axis and revolution about the tank axis for removing a low-boiling liquid component from the solution by evaporation. The organopolysiloxane used herein must become solid upon removal of a low-boiling liquid component by evaporation. More particularly, the method of the invention is advantageously applied to an organopolysiloxane which contains at least 10 mol %, especially at least 30 mol % of at least one of Q and T units, especially both and which becomes solid in the absence of a low-boiling liquid component, typically organic solvent. The remaining unit may be D unit and/or M unit.

The method of the invention is also applicable to an organopolysiloxane which remains liquid upon removal of a low-boiling liquid component by evaporation, for removing the low-boiling liquid component therefrom by evaporation. The method of the invention is especially advantageous to those organopolysiloxanes which have a higher molecular weight and a higher viscosity. Additionally, the invention is applicable to a slurry that organopolysiloxane powder forms with a non-solvent and a suspension in which organopolysiloxane powder is afloat on liquid because the powder can be recovered by evaporating and removing the liquid component. The invention is particularly advantageous when applied to fine powder having a mean particle size of less than 10 μm or powder which is difficult to separate by filtration and where more precise drying than the continuous drying as achievable by spray dryers is desired.

The low-boiling liquid component present in the organopolysiloxane solution is typically the solvent used in the synthesis of the organopolysiloxane, for example, aromatic hydrocarbons such as benzene, toluene and xylene, alcohols such as methanol, ethanol and propanol, ketones such as methyl ethyl ketone and methyl butyl ketone, and low molecular weight siloxanes such as hexamethyldisiloxane and octamethylcyclotetrasiloxane. The invention is applicable to any low-boiling liquid component having a boiling point which is sufficiently different from the intended organopolysiloxane to separate therefrom by simple distillation.

Figure 2:
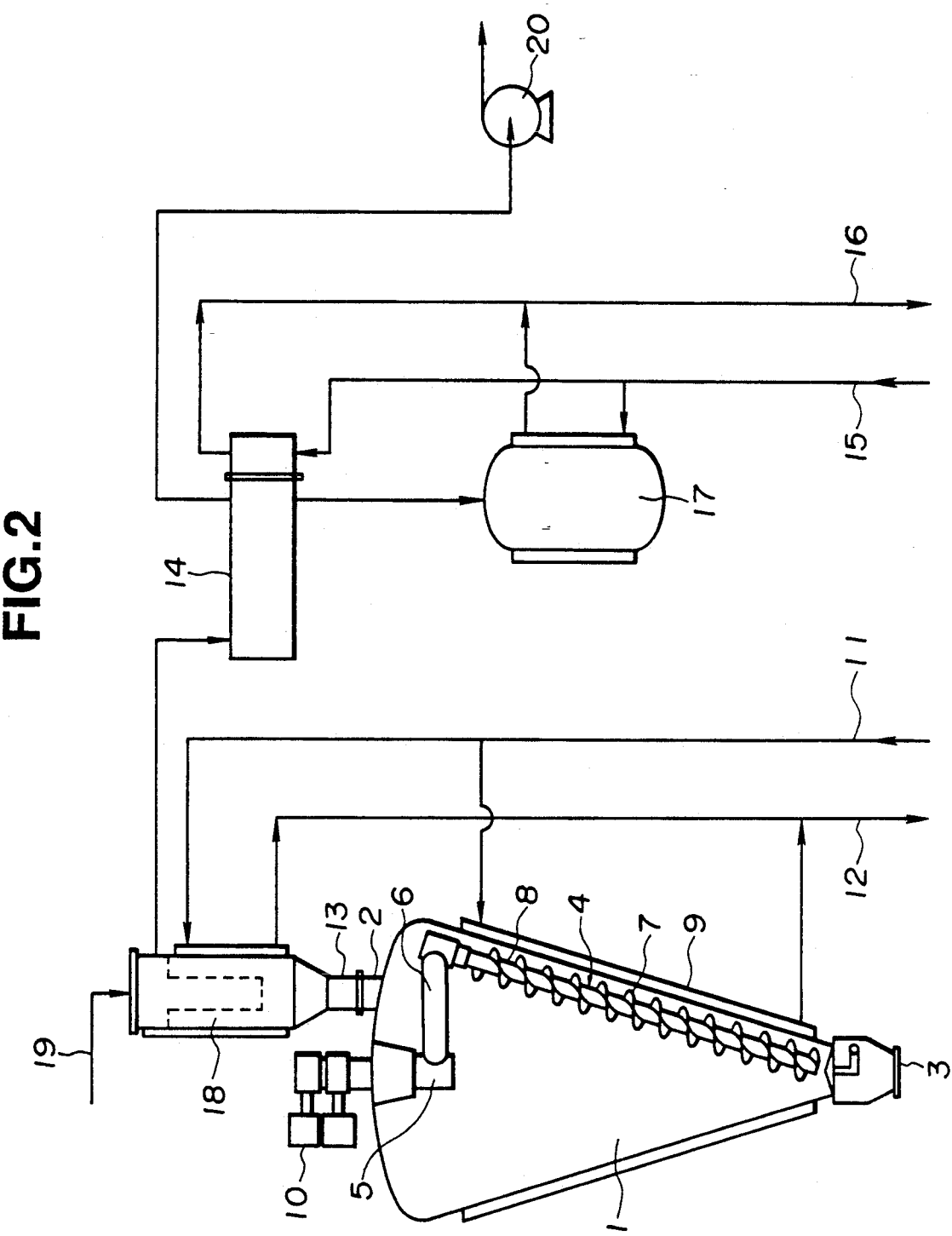
FIG. 2 schematically illustrates an overall system for practicing the method of the invention.

For obtaining organopolysiloxane powder, a system as shown in FIG. 2 may be used. The system includes the agitating tank 1 of FIG. 1 wherein an organopolysiloxane solution is heated and agitated while a low-boiling liquid component is separated therefrom by evaporation.

In operating the rotating shaft 8 or impeller 7 for providing agitation, the rotation of the shaft or impeller about its own axis is preferably 30 rpm or more, especially 40 to 150 rpm and the revolution of the shaft or impeller about the tank axis is preferably ½ rpm or more, especially 1 to 5 rpm, both for accomplishing sufficient mixing.

The tank 1 may be heated by feeding a hot medium, typically steam to the jacket 9 from a supply conduit 11, the medium being recovered through a return conduit 12. The heating medium through the jacket 9 should have a temperature above the boiling point of the low-boiling liquid component under the pressure prevailing in the tank. An electric heater may be used for heating instead of the heating jacket.

As a result of the heating/agitating procedure, the low-boiling liquid component will evaporate and escape from the tank 1 through the vent 2. The vapor is then channeled through a discharge conduit 13 and condensed in a condenser 14. The condenser 14 is cooled by feeding a coolant such as brine from a supply conduit 15 and returning it to a return conduit 16. The low-boiling liquid component which is condensed in the condenser 14 is collected in a reservoir 17. The reservoir 17 is also preferably cooled as is the condenser 14 because re-evaporation of the low-boiling liquid component therein is prevented. When the low-boiling liquid component vapor is discharged from the tank 1, powdered organopolysiloxane is scattered and entrained by the vapor and conveyed there-with into the discharge conduit 13, causing a lowering of the powder yield. For collecting such vapor-borne powder, a powder collector 18 in the form of a bag filter or cyclone is preferably disposed in the discharge conduit 13 between the vent 2 and the condenser 14. The collector 18 is a bag filter in the illustrated embodiment wherein compressed inert gas such as nitrogen gas is fed in pulses from a gas feed line 19 to the bag filter for back washing, thereby clearing off the powder and preventing the filter from clogging.

Evaporation of the low-boiling liquid component can be promoted by keeping the system in vacuum. To this end, a vacuum generator 20 in the form of a vacuum pump or steam ejector may be connected to the discharge conduit. Vacuum is produced in the tank 1 such that the boiling point of the low-boiling liquid component at that vacuum is lower than the temperature of the heating medium, preferably for establishing a difference of 50° C. or more between the boiling point of the low-boiling liquid component and the temperature of the heating medium.

As the low-boiling liquid component evaporates and separates from the organopolysiloxane solution in the tank, the solution increases in viscosity and sometimes tends to bubble. In the latter case, the temperature or vacuum may be properly controlled so as to prevent bumping.

The thus obtained organopolysiloxane powder is discharged from the tank 1 by gravity simply by opening a valve associated with the discharge port 3. A ball valve and plug valve are exemplary valves. A discharge controller in the form of a rotary valve may be provided where it is desired to control the discharge rate. Simply by locating the discharge port 3 at the bottom of the tank 1, the tank can be readily emptied of the powder.

EXAMPLE

Examples of the invention are given below by way of illustration and not by way of limitation.

EXAMPLE 1

A planetary-screw mixer (fixed tank type conical screw mixer, available as a SV mixer from Shinko Pantech K.K.) as shown in FIG. 1 was used. The mixer had an effective tank volume of 200 liters and was equipped with a motor of 5.5 kW for screw spinning and a motor of 0.2 kW for screw revolution. The screw was disposed parallel to the inner wall at an inclination angle of 17° relative to the vertical axis. The tank was charged with 100 kg of a siloxane resin solution consisting of 70% by weight of a siloxane resin having a M/Q unit molar ratio of 0.85 (M unit: $(CH_3)_3SiO_K$ unit, Q unit: $SiO_2$ unit) and 30% by weight of toluene. The solution was a clear colorless solution having a viscosity of 40 centipoise.

The mixer was installed in a system as shown in FIG. 2. The screw was rotated at 60 rpm about its own axis and revolved at 2 rpm in a planetary orbit about the tank axis. Heating was started by feeding steam at 4 kg/cm²G to the jacket. When the temperature in the mixing tank reached 60° C., the vacuum pump was actuated to start evacuation of the tank interior whereupon toluene started distilling out. Toluene vapor was condensed in a condenser for recovery.

With the mixing tank continuously heated, while observing bubbling in the tank, the degree of vacuum was gradually lowered such that no bumping occurred. The solution in the tank gradually increased its viscosity. When a pressure of 30 Torr and a temperature of 80° C. were reached in the tank, the contents in the tank turned solid. The powder which was scattered and conveyed together with the toluene vapor flow was collected by the bag filter disposed midway the vapor discharge conduit while the system continued to operate. The bag filter was cleaned every two minutes by reversely feeding nitrogen gas in pulses. Although aggregates were found at the initial point of time when the contents turned solid, the aggregates were ground as the operation continued, the contents resulting in white powder. The motors could continue operation for agitation without overload.

When a pressure of 5 Torr and a temperature of 130° C. were reached in the mixing tank, heating was interrupted and nitrogen gas was admitted into the tank interior until atmospheric pressure was resumed. The duration from the start to the end of heating was 4⅓ hours.

The valve at the tank bottom was opened to discharge the resulting powder. Simply by fully opening the valve, the tank could be completely emptied of the powder except for some deposits.

The powder was white and had a weight of 67 kg and a yield of 95.7%. A portion of the powder was heated in a dryer at 105° C. for 3 hours to determine a heat loss of 0.006% by weight.

COMPARATIVE EXAMPLE 1

An anchor agitator tank (vertical mixing tank plus anchor impeller) having an effective volume of 200 liters and equipped with a motor of 5.5 kW and an anchor impeller was charged with the same siloxane resin solution as in Example 1. The solution was agitated at 60 rpm. Heating was started by feeding steam at 4 kg/cm²G to the jacket. When the temperature in the mixing tank reached 60° C., the vacuum pump was actuated to start evacuation of the tank interior whereupon toluene started distilling out. Toluene vapor was condensed in a condenser for recovery.

With the mixing tank continuously heated, while observing bubbling in the tank, the degree of vacuum was gradually lowered such that no bumping occurred. The solution in the tank gradually increased its viscosity. When a pressure of 30 Torr and a temperature of 80° C. were reached in the tank, the motor stopped due to overloading.

With the motor stopped, the powder which was scattered and conveyed together with the toluene vapor flow was collected by the bag filter disposed midway the vapor discharge conduit while the system continued to operate. The contents turned solid, but formed a mass interfering with the agitating impeller against rotation. When a pressure of 5 Torr and a temperature of 130° C. were reached in the mixing tank, heating was interrupted and nitrogen gas was admitted into the tank interior until atmospheric pressure was resumed. The duration from the start to the end of heating was 8.5 hours.

The valve at the tank bottom was opened, but little of the solid discharged out. The mass was manually broken into fragments which fell down through the valve.

The solid product contained a multiplicity of aggregates in powder. Its weight was 52 kg with a yield of 74.3%. A portion of the powder was heated in a dryer at 105° C. for 3 hours to determine a heat loss of 0.2% by weight.

COMPARATIVE EXAMPLE 2

Using a spray dryer equipped with an electric heater having a power of 15 kW and a rotary disk atomizer, the same siloxane solution as used in Example 1 was sprayed at a rate of 22 kg/hour while feeding nitrogen gas heated at 150° C. White powder collected in a receiver below the spray dryer and was continuously taken out of the receiver. The system was operated for 4.5 hours until a throughput of 100 kg was reached. At this point, feed of the siloxane solution was stopped and the operation was interrupted.

The thus collected powder, combined with the powder collected in the cyclone, had a weight of 64 kg and a yield of 91.4%. A portion of the powder was heated in a dryer at 105° C. for 3 hours to determine a heat loss of 0.3% by weight.

As compared with Comparative Examples 1 and 2, Example 1 using a planetary-screw mixer produced a powder having a minimized residue of low-boiling liquid component. Example 1 had the advantages of elimination of motor interruption by overloading, a short processing time, and easy powder discharge from the tank as compared with Comparative Example 1. These results are shown in Table 1.

TABLE 1

|  | Example 1 | Comparative Example 1 | Comparative Example 2 |
|---|---|---|---|
| Apparatus | planetary-screw mixer | anchor agitator | spray dryer |
| Raw material | 70 wt % siloxane value (M/Q = 0.85) + wt % toluene | | |
| Evaporating time | 4⅓ hours | 8.5 hours | 4.5 hours |
| Motor operation | good | interrupted | — |
| Residual low-boiling liquid component | 0.006% | 0.2% | 0.3% |
| Discharge from tank | easy | difficult | easy |

EXAMPLE 2

A planetary-screw mixer as used in Example 1 was charged with 100 kg of a siloxane resin solution consisting of 50% by weight of a siloxane resin consisting of 100% T units which were $(CH_3)SiO_{3/2}$ units and 50% by weight of toluene. The solution was a clear colorless solution having a viscosity of 12 centipoise.

The screw was rotated at 60 rpm about its own axis and revolved at 2 rpm about the tank axis. Heating was started by feeding steam at 100° C. to the jacket. When the temperature in the mixing tank reached 40° C., the vacuum pump was actuated to start evacuation of the tank interior whereupon toluene started distilling out. Toluene vapor was condensed in a condenser for recovery.

With the mixing tank kept at 40° C., while observing bubbling in the tank, the degree of vacuum was gradually lowered such that no bumping occurred. The solution in the mixing tank gradually increased in viscosity. When the pressure in the mixing tank lowered to 30 Torr, the contents in the tank turned solid. The powder which was scattered and conveyed together with the toluene vapor flow was collected as in Example 1 while the system continued to operated. Although aggregates were found at the initial point of time when the contents turned solid, the aggregates were ground as the operation continued, the contents resulting in white powder. The motors could continue agitating operation without overload.

When a pressure of 5 Torr was reached in the mixing tank, heating was interrupted and nitrogen gas was admitted into the tank interior until atmospheric pressure was resumed. The duration from the start to the end of heating was 6.5 hours.

The valve at the tank bottom was opened to discharge the resulting powder. Simply by fully opening the valve, the tank could be completely emptied of the powder except for some deposits.

The powder was white and had a weight of 47 kg and a yield of 94.0%. A portion of the powder was heated in a dryer at 105° C. for 3 hours to determine a heat loss of 0.05% by weight.

It is evident from Examples 1 and 2 that organopolysiloxane powder can be produced whether the major units of organopolysiloxane are M and Q units or T units.

There has been described a method for producing free-flowing organopolysiloxane powder having a minimized content of a low-boiling liquid component within a relatively short time while requiring a relatively reduced motive power. The organopolysiloxane powder is characterized by a minimized content of a low-boiling liquid component and free flow or efficient removal from the tank.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing organopolysiloxane powder from an organopolysiloxane solution, comprising the steps of:
   admitting an organopolysiloxane solution into a generally conical hollow tank having a vertical center axis and an inner wall, said tank being equipped with agitating means including a rotating shaft having at least one impeller positioned at an inclination in close proximity to the tank inner wall, said agitating means being effective for driving said shaft such that said shaft may rotate about its own axis and revolve about the center axis of the tank along the tank inner wall, and
   operating said agitating means for agitating the solution by rotation and revolution of said rotating shaft at a sufficient temperature to allow a low-boiling liquid component to evaporate from the solution, thereby evaporating and removing the low-boiling liquid component from the solution.

2. The method of claim 1 wherein said tank is of inverted conical shape.

3. The method of claim 1 wherein said rotating shaft has a screw shaped impeller 4. The method of claim 1 wherein said rotating shaft has a plurality of impellers 5. The method of claim 1 wherein said organopolysiloxane includes at least one of units represented by the following general formulae (1) and (2):

| | |
|---|---|
| $SiO_2$ | (1) |
| $RSiO_{3/2}$ | (2) | wherein R is independently a hydrogen atom or a substituted or unsubstituted monovalent hydrocarbon group.

6. The method of claim 1, wherein the inclination of the rotating shaft is about 10° to 30° with respect to the vertical center axis of the tank.

7. The method of claim 5, wherein the organopolysiloxane includes at least 10 mol % of at least one of the units represented by formulae (1) and (2).

8. The method of claim 5, wherein the organopolysiloxane includes at least 30 mol % of at least one of the units represented by formulae (1) and (2).

9. The method of claim 1, wherein the organopolysiloxane becomes a solid in the absence of the low-boiling liquid component which is removed.

* * * * *